(12) United States Patent
Mendiratta et al.

(10) Patent No.: US 9,708,365 B2
(45) Date of Patent: Jul. 18, 2017

(54) PURIFICATION PROCESS FOR MONOCLONAL ANTIBODIES

(71) Applicant: Cadila Healthcare Limited, Ahmedabad (IN)

(72) Inventors: Sanjeev Kumar Mendiratta, Ahmedabad (IN); Sanjay Bandyopadhyay, Ahmedabad (IN); Avanish Kumar Singh, Ahmedabad (IN)

(73) Assignee: Cadila Healthcare Limited, Ahmedabad Gujarat (IN)

( * ) Notice: Subject to any disclaimer, the term of this patent is extended or adjusted under 35 U.S.C. 154(b) by 0 days.

(21) Appl. No.: 14/895,432

(22) PCT Filed: Jun. 25, 2014

(86) PCT No.: PCT/IN2014/000421
§ 371 (c)(1),
(2) Date: Dec. 2, 2015

(87) PCT Pub. No.: WO2014/207763
PCT Pub. Date: Dec. 31, 2014

(65) Prior Publication Data
US 2016/0115195 A1 Apr. 28, 2016

(30) Foreign Application Priority Data
Jun. 25, 2013 (IN) .......................... 2145/MUM/2013

(51) Int. Cl.
| | | |
|---|---|---|
| C07K 1/36 | (2006.01) | |
| C07K 1/20 | (2006.01) | |
| C07K 1/22 | (2006.01) | |
| C07K 16/06 | (2006.01) | |
| C07K 16/24 | (2006.01) | |
| C07K 16/28 | (2006.01) | |
| C07K 16/32 | (2006.01) | |

(52) U.S. Cl.
CPC .............. *C07K 1/36* (2013.01); *C07K 16/065* (2013.01); *C07K 16/241* (2013.01); *C07K 16/2863* (2013.01); *C07K 16/2887* (2013.01); *C07K 16/32* (2013.01); *C07K 2317/21* (2013.01); *C07K 2317/24* (2013.01)

(58) Field of Classification Search
None
See application file for complete search history.

(56) References Cited

U.S. PATENT DOCUMENTS

| | | | | |
|---|---|---|---|---|
| 5,641,870 A | * | 6/1997 | Rinderknecht | ...... C07K 16/065 435/252.3 |
| 2010/0135987 A1 | * | 6/2010 | Hickman | ............... C07K 16/00 424/130.1 |
| 2011/0097340 A1 | * | 4/2011 | Ramachandra | ........ C07K 16/22 424/158.1 |
| 2012/0264920 A1 | * | 10/2012 | Wang | ................... B01D 15/125 530/388.1 |
| 2013/0260419 A1 | * | 10/2013 | Ransohoff | .............. C12M 47/10 435/69.6 |
| 2014/0128577 A1 | * | 5/2014 | Kulkarni | ............ C07K 14/7151 530/387.3 |
| 2014/0288278 A1 | * | 9/2014 | Nti-Gyabaah | ..... B01D 15/3809 530/388.24 |
| 2016/0024144 A1 | * | 1/2016 | Trejo | ................. C07K 14/7151 530/387.3 |
| 2016/0083453 A1 | * | 3/2016 | Hunter | ................. C07K 16/065 530/387.3 |

FOREIGN PATENT DOCUMENTS

| | | | | |
|---|---|---|---|---|
| WO | WO 9522389 A1 | * | 8/1995 | ........... B01D 15/327 |
| WO | WO 9962936 A1 | * | 12/1999 | ............... C07K 1/18 |
| WO | WO-2013/066707 A1 | | 5/2013 | |

OTHER PUBLICATIONS

International Application No. PCT/IN2014/000421, International Preliminary Report on Patentability mailed Sep. 7, 2015, 18 pgs.
International Application No. PCT/IN2014/000421, International Search Report mailed Nov. 27, 2014, 3 pgs.
International Application No. PCT/IN2014/000421, Written Opinion of the International Preliminary Examining Authority mailed Jun. 8, 2015, 5 pgs.
International Application No. PCT/IN2014/000421, Written Opinion of the International Search Authority mailed Nov. 27, 2014, 4 pgs.
Chen, J., et al., "Comparison of standard and new generation hydrophobic interaction chromatography resins in the monoclonal antibody purification process", Journal of Chromatography A, 1177, (2008), 272-281.

\* cited by examiner

*Primary Examiner* — Daniel E Kolker
*Assistant Examiner* — James Rogers
(74) *Attorney, Agent, or Firm* — Schwegman Lundberg & Woessner, P.A.

(57) ABSTRACT

The present invention provides an improved method for the purification of monoclonal antibody from cell culture. Process of purification of the desired monoclonal antibody comprises affinity, hydrophobic interaction and optionally ion exchange column chromatography. It provides more than 99% purity of the desired monoclonal antibody.

34 Claims, 9 Drawing Sheets

PURIFICATION PROCESS FOR MONOCLONAL ANTIBODIES

CLAIM OF PRIORITY

This application is a U.S. National Stage Filing under 35 U.S.C. 371 from International Application No. PCT/IN2014/000421, filed on Jun. 25, 2014, and published as WO 2014/207763 A1 on Dec. 31, 2014, which claims the benefit of priority under 35 U.S.C. §119 to Indian Provisional Patent Application No. 2145/MUM/2013, filed on Jun. 25, 2013, which are hereby incorporated by reference herein in their entireties.

FIELD OF THE INVENTION

The present invention provides an improved method for the purification of monoclonal antibody from cell culture. Process of purification of the desired monoclonal antibody comprises affinity, hydrophobic interaction and optionally ion exchange column chromatography. It provides more than 99% purity of the desired monoclonal antibody.

BACKGROUND OF THE INVENTION

Purification of pharmaceutical grade monoclonal antibody protein from cell culture media includes harvest/clarification followed by purification by using a series of column chromatography steps in combination with membrane ultrafiltration and diafiltration. After purification, the desired antibody preparation is suitably formulated and stored in appropriate conditions. However, many times, these steps do not provide the antibody with the desired level of purity and quality that are required for their pharmaceutical use. Sometimes, process-related and product-related impurities are observed to co-elute with the desired antibody during column purification. Therefore, it is important to reduce or remove such impurities from the desired preparation. Moreover, protein aggregation is a major concern during monoclonal antibody (mAb) production. The presence of aggregates can reduce the therapeutic efficacy of monoclonal antibody and known to trigger immunogenic responses in humans. Therefore, it is necessary to remove aggregates from the desired preparation of monoclonal antibody during downstream purification, mainly by column chromatography. With an aim to resolve this problem, the present invention provides novel method of purification of antibodies, which helps in the removal of process- and product-related impurities along with high molecular weight aggregates up to the desired level from a cell-free culture medium containing the antibody of interest by using a series of column chromatography in a particular manner. In the current invention, the said process of purification of antibody demonstrates well-controlled process of purification in a straight-forward manner which yields to a highly purified preparation of antibody with more than 80% recovery. In the current invention, the highly purified preparation of an antibody means a preparation of antibody with at least 99% purity and substantially free of process- and product related impurities and essentially devoid of high molecular weight aggregates of protein. Furthermore, the current invention provides a highly scalable and reproducible process of purification of monoclonal antibody. The described novel process of purification provides a common platform for purification of various antibodies for therapeutic use, in terms of process economy and industry viability.

Some of such techniques are disclosed in following patents:

U.S. Pat. No. 6,417,335 discloses method for purifying an antibody from a composition comprising the antibody and a contaminant, which method comprises: (a) loading the composition onto a cation exchange resin, wherein the amount of antibody loaded onto the cation exchange resin is from about 20 mg to about 35 mg of the antibody per mL of cation exchange resin; and (b) eluting the antibody from the cation exchange resin.

U.S. Pat. No. 7,863,426 describes method for producing a host cell protein-(HCP) reduced antibody preparation from a mixture comprising an antibody and at least one HCP, comprising an ion exchange separation step wherein the mixture is subjected to a first ion exchange material, such that the HCP-reduced antibody preparation is obtained.

Other relevant patents of the present field of invention are U.S. Pat. No. 6,489,447 EP 1075488; EP1308455; EP1308456B etc. Each of which are incorporated as reference in their entirety.

The present invention provides a novel purification process of antibodies by employing the conventional column chromatography techniques in a unique manner to obtain a highly purified preparation of desired antibody while removing the process- and product-related impurities especially the protein aggregates. We herein disclose such a purification process.

SUMMARY OF THE INVENTION

The present invention provides a method for purifying monoclonal antibody from cell culture derived crude mixture.

In one aspect, the present invention provides a process for purification of monoclonal antibody from a crude mixture comprising a series of chromatography and ultrafiltration-diafiltration steps.

In another aspect, the present invention provides a process of purification of monoclonal antibody from a crude mixture comprising use of a Protein A affinity chromatography and a hydrophobic interaction chromatography steps. Protein G or protein L can be used as column matrix in the affinity chromatography step.

In a further aspect, Protein A affinity chromatography step includes loading of a crude mixture containing the desired antibody to the column at suitable pH and/or conductance for binding, followed by column wash prior to elution of the desired antibody in the form of a single peak.

In another aspect, the process according to the present invention includes three column wash steps wherein (i) First wash with equilibration buffer, (ii) Second wash at the same pH and/or a conductivity higher than the first wash buffer (iii) Third wash at a pH and/or a conductivity lower than the second wash (iv) Elution of an antibody at lower pH and/or higher conductivity than third wash.

In another aspect, hydrophobic interaction chromatography according to the present invention is performed with down-the-gradient salt concentration.

In a further aspect, the present invention provides a purification process of monoclonal antibody from crude mixture comprising a Protein A chromatography, a hydrophobic interaction chromatography and an ion exchange column chromatography.

In yet another aspect, the present invention provides a purification process of monoclonal antibody from crude mixture comprising a Protein A chromatography, a hydrophobic interaction chromatography and an ion exchange column chromatography in combination with ultrafiltration-diafiltration for reconditioning of the protein solution. Protein solution termed here as either a mixture of contaminating proteins and the desired antibody or a relatively pure preparation of desired antibody obtained through the process described herein.

In a further aspect, ion exchange chromatography according to the present invention is selected from cation exchange chromatography and anion exchange chromatography, preferably anion exchange chromatography.

In a preferred embodiment, the present invention provides a purification process of monoclonal antibody comprising the following steps:
1. Protein A chromatography
2. Hydrophobic interaction chromatography
3. Anion exchange chromatography The hydrophobic interaction chromatography and anion exchange chromatography steps may be carried out in any order.

Protein A column step is useful to capture the monoclonal antibody from crude mixture and to elute the desired monoclonal antibody from the column with high level of purity in bind-elute mode. Hydrophobic interaction chromatography step is used for further removal of process- and product-related impurities in bind-elute mode. Anion exchange chromatography is employed for further removal of process-related impurities in flow-through mode.

In one of the aspects, the antibodies which can be purified according to the present invention include anti-HER2 antibody, anti-TNF alpha antibody, anti-VEGF antibody, anti-CD20 antibody, anti-CD52, anti-RANKL, anti-IgE antibody, etc.

In further aspects, the present invention provides an antibody preparation with an amount of aggregates no greater than 5% after protein A affinity chromatography step.

In another aspect, the present invention provides an antibody preparation with an amount of aggregates no greater than 1%, more preferably no greater than 0.5%.

The abbreviations used in the present description are defined below:
Protein A: Protein A cross-linked agarose column.
HIC: Hydrophobic interaction column chromatography.
AEX: Anion exchange column chromatography.
HP-SEC: High performance-size exclusion chromatography.
MWCO: Molecular weight cut-off.
NaCl: Sodium chloride.
WFI: Water for Injection.

BRIEF DESCRIPTION OF THE FIGURES AND TABLES

DETAILED DESCRIPTION OF THE INVENTION

Figure 1:
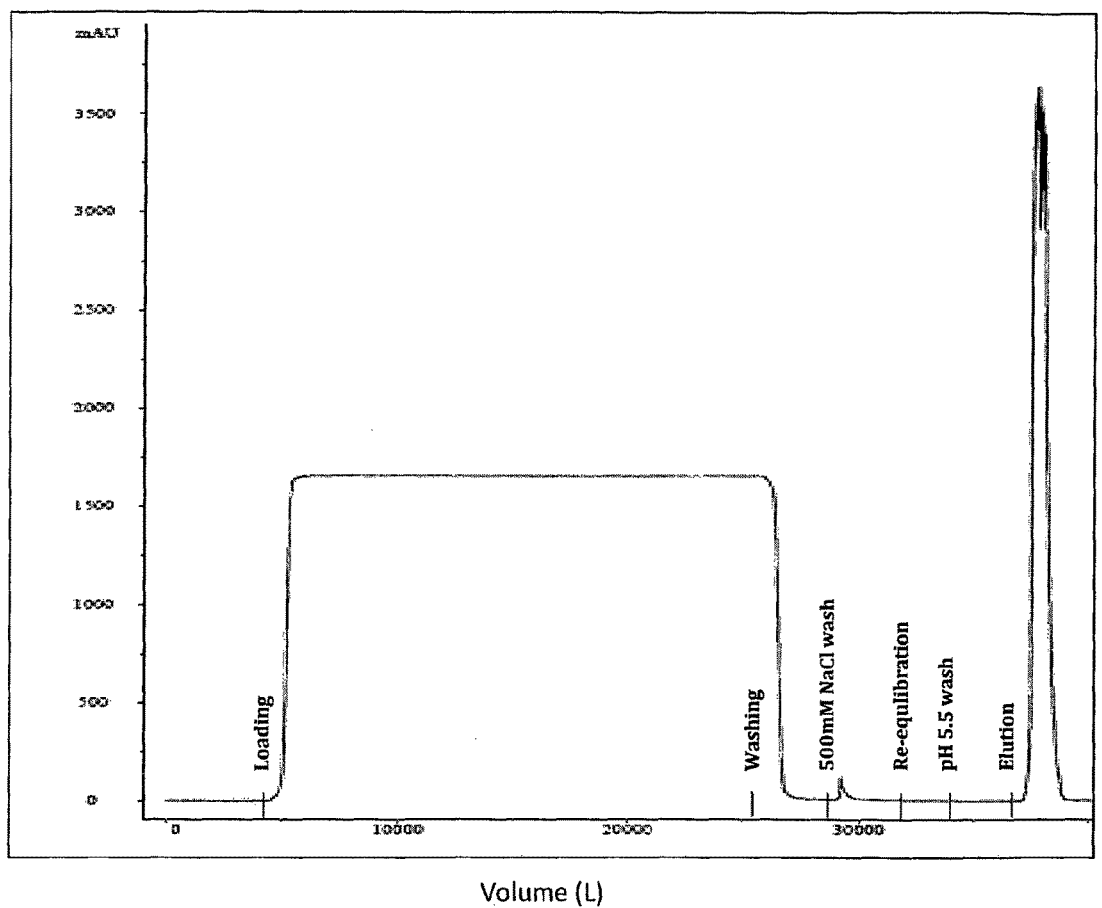
FIG. 1 illustrates elution profile of adalimumab through Protein A affinity column chromatography.

The present invention describes the purification process of cell-culture derived monoclonal antibody by using a series of column chromatography steps comprising an affinity column, a hydrophobic interaction column and an ion exchange column chromatography in combination with ultrafiltration and diafiltration.

In one of the embodiments, the present invention provides a purification process of cell culture derived monoclonal antibody from a crude mixture by using a Protein A column chromatography, first to capture, and then elute the protein from the column with high level of purity at low pH optionally in the presence of additives/salts. Crude mixture may include host-cell derived contaminating proteins, product-related substances and other impurities in addition to that of the protein of interest. Protein G or protein L can be used as column matrix in the affinity chromatography step.

In another embodiment, the process according to the present invention includes three column wash steps wherein (i) First wash with equilibration buffer (ii) Second wash at the same pH and/or a conductivity higher than the first wash buffer (iii) Third wash at a pH and/or a conductivity lower than the second wash (iv) Elution of an antibody at lower pH and/or higher conductivity than third wash.

In a preferred embodiment, column wash steps according to the present invention comprising: (i) First wash with equilibration buffer at about pH 7.4 and/or conductivity about 20 mS/cm, preferably in the range of 1 mS/cm to 30 mS/cm (ii) Second wash at about pH 7.4 and/or conductivity more than 20 mS/cm (iii) Third wash at lower pH than pH 7.4, preferably in the range of pH 5 to pH 6.5 and/or conductivity less than 20 mS/cm, preferably in the range of 1 mS/cm to 5 mS/cm (iv) Elution of an antibody at about pH 3.5 and/or conductivity higher than 5 mS/cm.

In one of the embodiments, the buffer component for protein A chromatography purification step is selected from Tris, acetate and citrate buffer.

In a preferred embodiment, elution of an antibody according to the current invention is performed at a pH ranging from about pH 3.5 to 4, preferably 3.5 to 3.7.

In one of the embodiments, the process according to the present invention includes additives/salts selected from sodium chloride, arginine, glycine, preferably sodium chloride.

The present invention also demonstrates the removal of majority of the host cell contaminating proteins by Protein A column chromatography while eluting the protein of interest out of the column at low buffer pH condition in the presence of salt with maximum recovery.

In one of the embodiments, the present invention also demonstrates that the molecular integrity of the desired monoclonal antibody after elution from Protein A column, under acidic pH conditions remain unaltered for at least about 1 hour, as assessed by analytical HP-SEC.

In another embodiment, the present invention provides the removal of residual process-related and product-related impurities from the desired protein fraction by using a hydrophobic interaction column chromatography in bind-elute mode. Elution of the desired protein is performed with down-the-gradient salt concentration in the form of a major peak.

In further embodiment, the column matrix for hydrophobic interaction chromatography is selected from phenyl sepharose, butyl sepharose, octyl sepharose, preferably, phenyl sepharose.

In furthermore embodiment, the salt for elution of the desired protein at hydrophobic interaction chromatography step is selected from ammonium sulphate, sodium chloride, ammonium chloride and sodium sulphate preferably, ammonium sulphate.

In another embodiment, hydrophobic interaction chromatography is performed at pH in the range of pH 5 to pH 7 and/or conductivity more than 100 mS/cm.

In one of the embodiments, ion exchange chromatography according to the present invention is selected from cation exchange chromatography and anion exchange chromatography, preferably anion exchange chromatography.

In another embodiment, column matrix for anion exchange chromatography step is selected from DEAE sepharose, Mono Q and Q sepharose XL, preferably Q sepharose.

In one of the embodiments, the present invention also illustrates purification of the desired monoclonal antibody in flow-through-and-wash mode through an anion exchange column chromatography or bind-elute mode through cation exchange chromatography.

In a preferred embodiment, purification of the desired monoclonal antibody derived from cell culture is carried out as follows:
1. Protein A chromatography
2. Hydrophobic interaction chromatography
3. Anion exchange chromatography The hydrophobic and anion exchange chromatography steps can be performed in any order after the Protein A column chromatography steps.

In a preferred embodiment, purification of the desired monoclonal antibody derived from cell culture is performed as follows—
1. Protein A chromatography
2. Low-pH incubation
3. Neutralization and reconditioning
4. Hydrophobic interaction chromatography
5. Ultrafiltration-diafiltration
6. Anion exchange chromatography
7. Nano-filtration
8. Ultrafiltration-diafiltration Wherein the hydrophobic chromatography, ultrafiltration-diafiltration and anion exchange chromatography steps can be performed in any order after the Protein A chromatography step.

In further embodiment, diafiltration medium is selected from water, citrate buffer, phosphate buffer, succinate buffer, acetate buffer and combination thereof.

In one of the embodiments, recovery of antibody from the column, according to the current invention is performed with additive/salt selected from sodium chloride, arginine, glycine, preferably sodium chloride.

In one of the embodiments, the overall recovery of an antibody according to the current invention is in the range of not less than 50%, preferably, not less than 70%, more preferably, in the range of 85% to 90% of the initial amount.

In a preferred embodiment, the antibody is selected from anti-HER antibody, anti-TNF antibody, anti-VEGF antibody, anti-CD20 antibody, anti-CD52 antibody, anti-RANKL, anti-IgE antibody, etc.

In a more preferred embodiment, the antibody is selected from trastuzumab, pertuzumab, infliximab, adalimumab, bevacizumab, ranibizumab, rituximab, bectumomab, epratuzumab, etc.

In further embodiment, the present invention provides purified antibody preparation with an amount of aggregates no greater than 5%, preferably no greater than 2% after protein A affinity chromatography step.

In another embodiment, the present invention provides an antibody preparation with an amount of aggregates no greater than 1%, more preferably no greater than 0.5%.

Purification process of the desired monoclonal antibody comprises the following steps—
  Cell separation and clarification of the culture supernatant by centrifugation and depth-filtration followed by reconditioning
  Protein A column chromatography
  Low-pH incubation
  Neutralization and reconditioning
  Hydrophobic interaction column chromatography
  Ultrafiltration-diafiltration
  Anion exchange column chromatography
  Nano-filtration
  Ultrafiltration-diafiltration
  Microfiltration The steps of purification according to the present invention are described in further details below:
I) Protein a Column Chromatography:
  Cell culture derived clarified supernatant containing the desired monoclonal antibody and other contaminants is loaded on to a Protein A column equilibrated with a suitable buffer at a pH close to neutrality. The desired monoclonal antibody binds to the affinity matrix, whereas majority of the contaminants pass out of the column in the flow-through. Prior to the elution of the desired protein, the column is washed with a plurality of wash steps. The first wash is performed after the completion of column-loading with the same equilibration buffer. The second wash is performed with a buffer of the same pH having higher conductivity than that of the first wash buffer. The third wash is carried out at a different pH and conductivity buffer than that of the first and second wash steps. Elution of the desired protein is carried out at pH lower than that of the third wash step, but at higher conductance. Finally, column cleaning is performed with an alkaline solution.

II) Hydrophobic Interaction Column Chromatography:
  Purification of the desired monoclonal antibody protein from a mixture containing at least one undesired contaminant is conducted by hydrophobic interaction column chromatography in bind-elute mode. After completion of protein-loading on to the column, the desired monoclonal antibody is eluted from the column with down-the-gradient salt concentration i.e. with decreased conductivity compared to that of the equilibration buffer conductivity. Elution of the desired monoclonal antibody protein takes place in the form of a single broad peak. The eluted protein is collected in fractions and the fractions containing the desired level of purity are pooled together.

III) Anion Exchange Column Chromatography:

Protein solution containing the desired monoclonal antibody is reconditioned substantially to match up to the pH and conductivity of the anion exchange column equilibration condition. Column is equilibrated with a buffer of pH about 6.5. The desired protein is recovered from the column in the flow-through-and-wash fraction. For carrying out anion exchange chromatography according to the present invention, other anion exchangers which also can be used are selected from DEAE sepharose, Mono Q, Q sepharose XL, and the like. Anion exchanger Q sepharose has been used in the present invention.

Analytical Technique:

Analytical size-exclusion chromatography (HP-SEC) is performed by using a TSK-3000 column equilibrated with sodium phosphate buffer of pH 6.8 in the presence of 300 mM NaCl. Protein is eluted in an isocratic-mode at 0.5 mL/min.

EXAMPLES

Here, the present invention is illustrated with the following non-limiting examples which should not be interpreted as limiting the scope of the invention in any way:

Example 1: Purification of Adalimumab (Anti-TNFα Antibody)

Step 1: Cell Separation/Clarification/Reconditioning

After harvesting the batch, cells were separated from the culture broth, first by centrifugation followed by depth filtration in order to obtain clear supernatant containing the protein of interest along with other soluble contaminants. Centrifugation was carried out at 10,000 g×30 minutes. Depth filtration was performed by using 0.45→0.22 µm membrane. The clarified supernatant was reconditioned to tune up with the Protein A column equilibration buffer condition for pH and conductance.

Step 2: Protein a Column Chromatography

Figure 2:
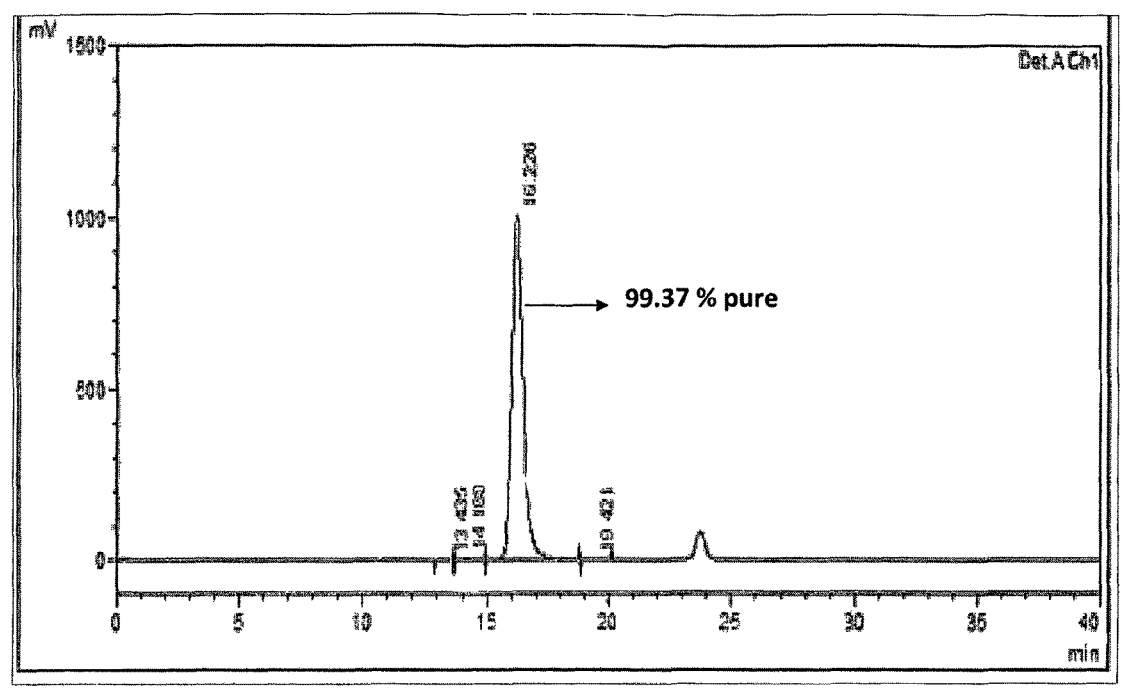
FIG. 2 illustrates the purity of the Protein A affinity purified adalimumab by analytical HP-size exclusion chromatography (HP-SEC). The figure shows that more than 99% purity of adalimumab is achieved after first column purification.

The clarified supernatant after reconditioning was passed through a Protein A affinity column to capture adalimumab by the affinity matrix followed by its elution from the column at low pH. Prior to loading, the column was equilibrated with a suitable buffer of pH 7.4 at a conductance in the range of 10-25 mS/cm. Subsequent to loading, the column was washed with the same buffer (first wash). Following the first wash step, the column was washed with the same buffer of pH 7.4 but at higher conductance (>25 mS/cm). A third wash step was performed with a suitable buffer of pH 5.5 having a conductance in the range of 1-5 mS/cm. After the third wash step, elution of the desired protein, adalimumab was conducted with a suitable buffer of pH 3.5-3.7 at a conductance greater than 5 mS/cm, as shown in FIG. 1. Adalimumab eluted after this step shows at least 98% purity when analyzed by analytical HP-SEC shown in FIG. 2.

Step 3: Low-pH Incubation

Protein A column-eluted desired protein fraction was incubated at the same elution pH condition for about 45-60 min under room temperature condition for viral inactivation, after which the protein solution was passed through a 0.22 µm filter.

Step 4: Neutralization and Reconditioning

Following low-pH treatment, neutralization step was performed with the addition of alkaline solution in a controlled manner. The protein solution was reconditioned with the adjustment of pH and conductance by UF/DF using 30 kDa MWCO membrane filter to match up to the next column equilibration conditions. For adjustment of conductance, concentrated ammonium sulfate solution was added to the protein solution. After reconditioning, protein solution was passed through 0.22 µm membrane filter and loaded on to a hydrophobic interaction column.

Step 5: Hydrophobic Interaction Column Chromatography

Figure 3:
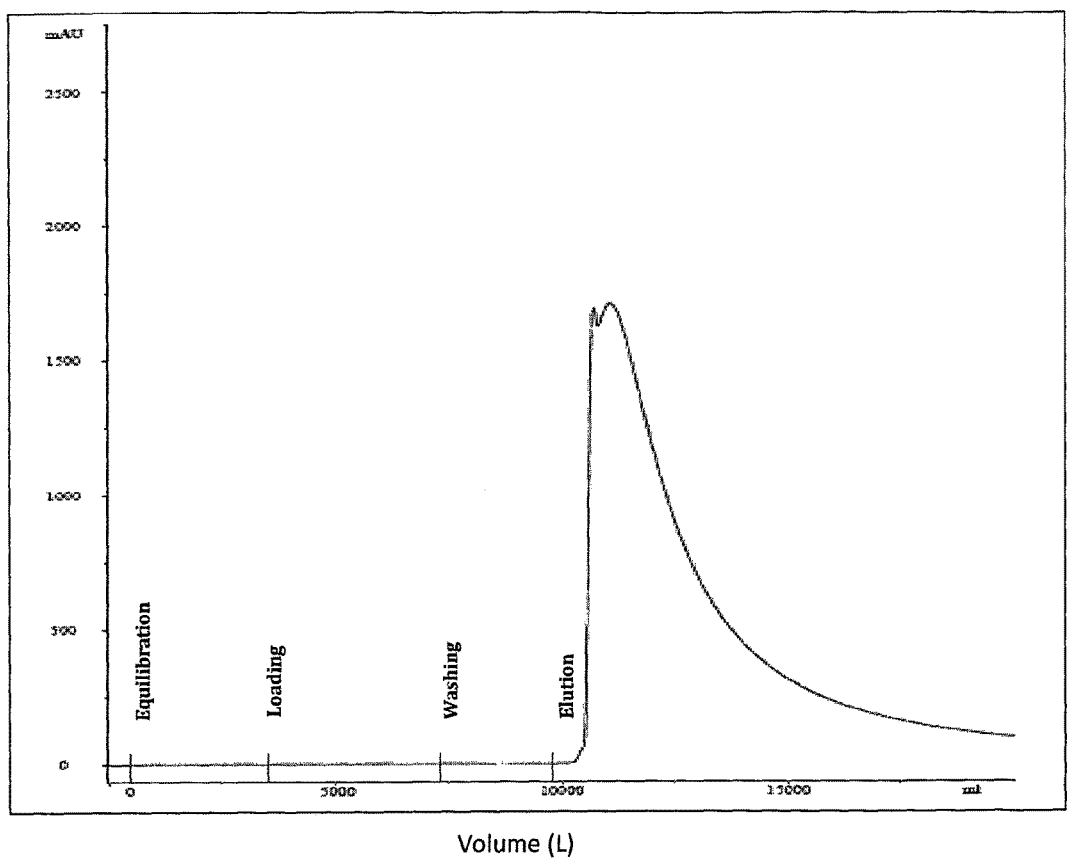
FIG. 3 illustrates the elution profile of adalimumab through hydrophobic interaction column chromatography.
Figure 4:
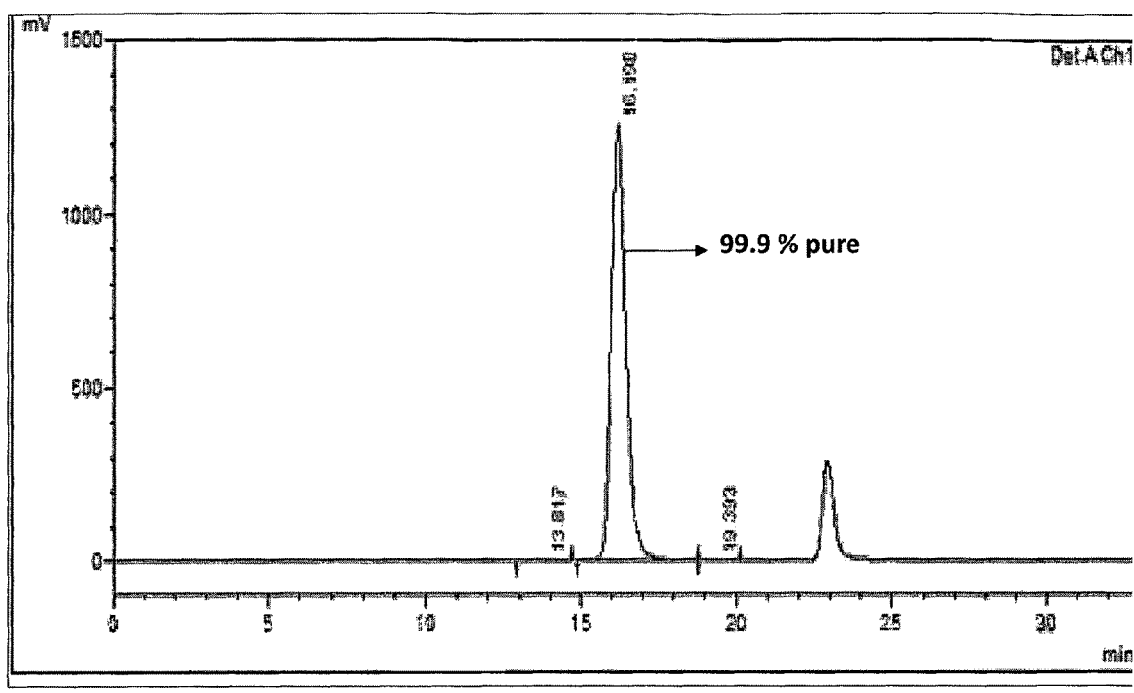
FIG. 4 illustrates the purity of the HIC purified adalimumab by analytical HP-size exclusion chromatography (HP-SEC). The figure shows that more than 99% purity of adalimumab is achieved after second column purification.

After reconditioning, the protein solution containing adalimumab was passed through hydrophobic interaction chromatography matrix, phenyl sepharose, for further purification in bind-elute mode. The column was equilibrated with a suitable buffer of pH about 6.5 to pH 7.0 having a conductance more than 90 mS/cm. Following binding to the column matrix, adalimumab was eluted from the column in the same buffer with down the salt gradient, as shown in FIG. 3. More than 99% purity of adalimumab is achieved after this column step, as assessed by HP-SEC shown in FIG. 4.

Step 6: Ultrafiltration-Diafiltration (UF/DF)

The hydrophobic column-eluted pooled fraction was reconditioned, substantially, by UF/DF using 30 kDa MWCO membrane filter against low ionic strength Na-citrate buffer solution of pH 6.5 in order to match to equilibration buffer conditions (e.g. pH and conductance) of the next column (Q column) step. Diafiltered protein solution was passed through a 0.22 µm filter and loaded on to a Q-column.

Step 7: Anion Exchange Column Chromatography

Figure 5:
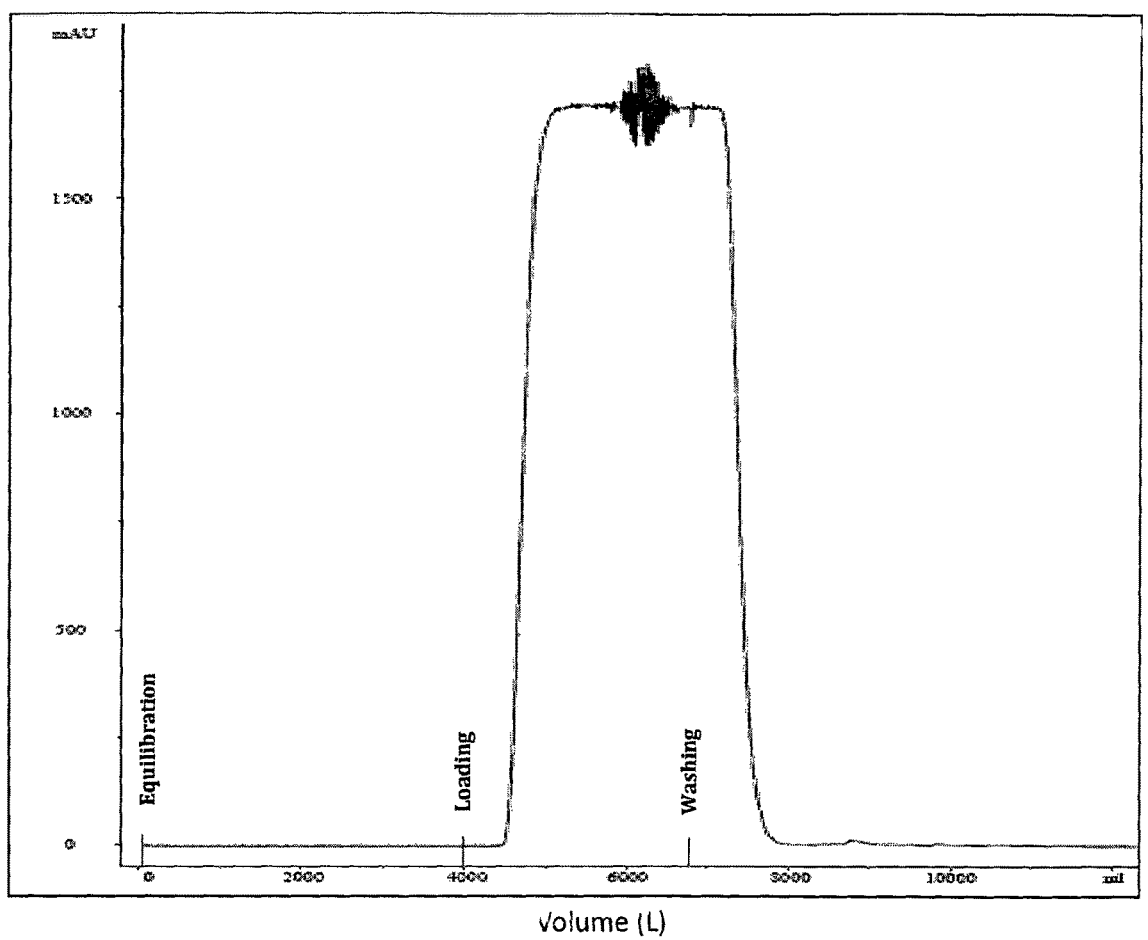
FIG. 5 illustrates the anion exchange column chromatography profile of the adalimumab.
Figure 6:
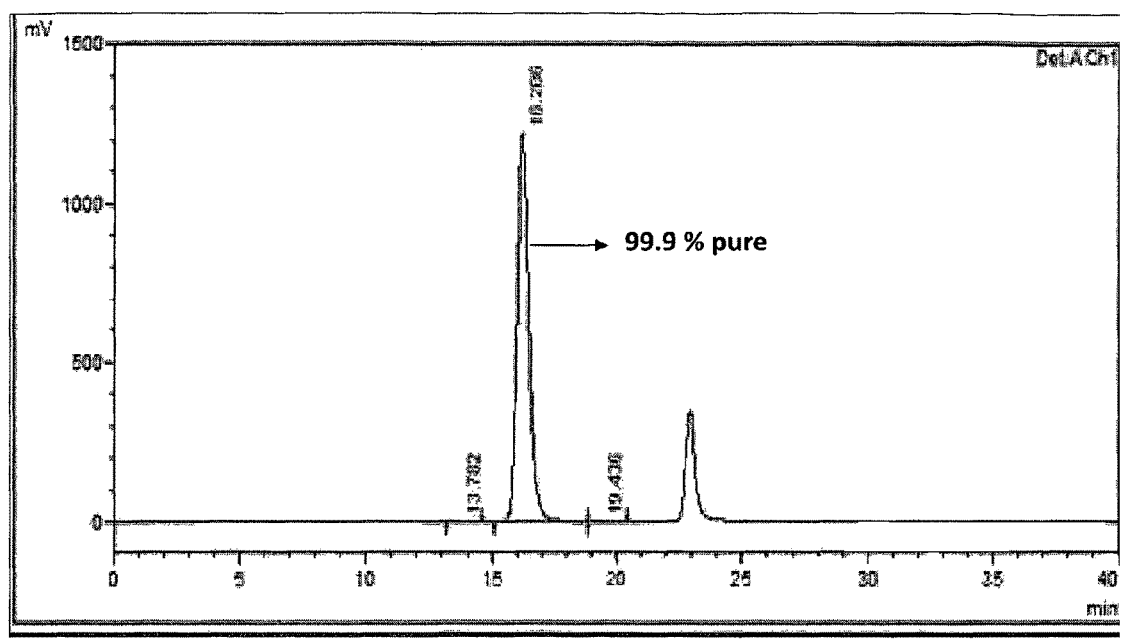
FIG. 6 illustrates the purity of the AEX column purified adalimumab by analytical HP-size exclusion chromatography (HP-SEC). The figure shows that more than 99% purity of adalimumab is achieved after AEX column purification.

Diafiltered protein solution containing the desired monoclonal antibody was passed through a Q-sepharose column in flow-through-and-wash mode with a suitable buffer of pH 6.5 at conductance below 10 mS/cm, as shown in shown in FIG. 5. After the Q-column step, purity of adalimumab is observed to be >99%, as assessed by HP-SEC shown in FIG. 6.

Step 8: Nano-Filtration

After the Q-column step, the protein solution containing the desired monoclonal antibody underwent a nano-filtration step. After nano-filtration, purity of adalimumab is observed to remain more than 99%.

Step 9: Ultrafiltration-Diafiltration

After nano-filtration, protein solution was diafiltered with desired media for the preparation of bulk drug substance.

Step 10: Microfiltration

Figure 7:
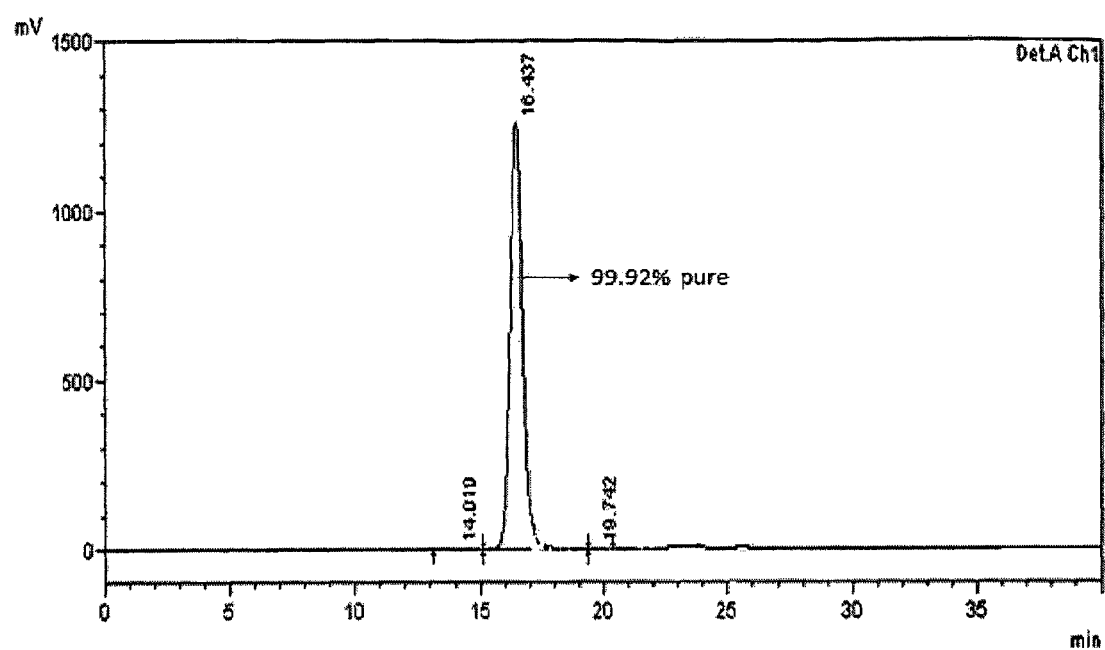
FIG. 7 illustrates the purity of the purified adalimumab by analytical HP-size exclusion chromatography (HP-SEC). The figure shows that more than 99% purity of adalimumab is achieved at the end of purification in the final preparation.

Finally, the purified preparation containing the desired monoclonal antibody was passed through 0.22 µm membrane filter, aseptically, and was stored either in the liquid form, under cold condition or under frozen condition for storage. The concentration of protein in the final preparation may vary from 1 mg/mL to 60 mg/mL. The final purified monoclonal antibody adalimumab exhibits more than 99% purity, as assessed by HP-SEC shown in FIG. 7.

Example 2: Purification of Rituximab (Anti-CD20 Antibody)

Figure 8:
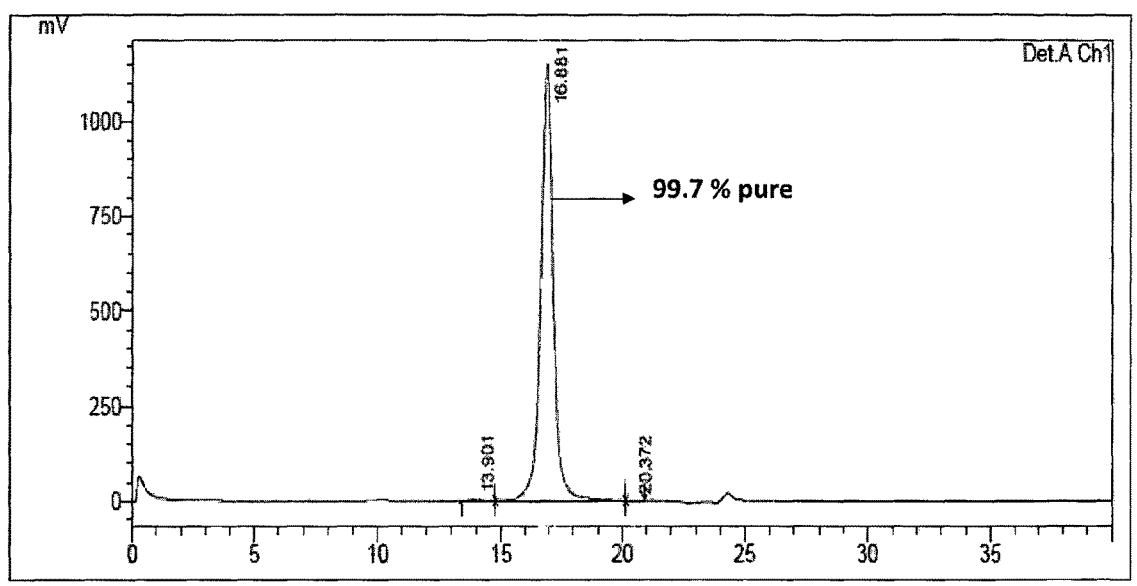
FIG. 8 illustrates the purity of the HIC purified rituximab by analytical HP-size exclusion chromatography (HP-SEC). The figure shows that more than 99% purity of rituximab is achieved after second column purification.

The purification process for anti-CD20 antibody, Rituximab, was carried out in the manner as described in example 1. The final purified monoclonal antibody exhibits more than 99% purity, as assessed by HP-SEC shown in FIG. 8.

Example 3: Purification of Trastuzumab
(Anti-HER2 Antibody)

Figure 9:
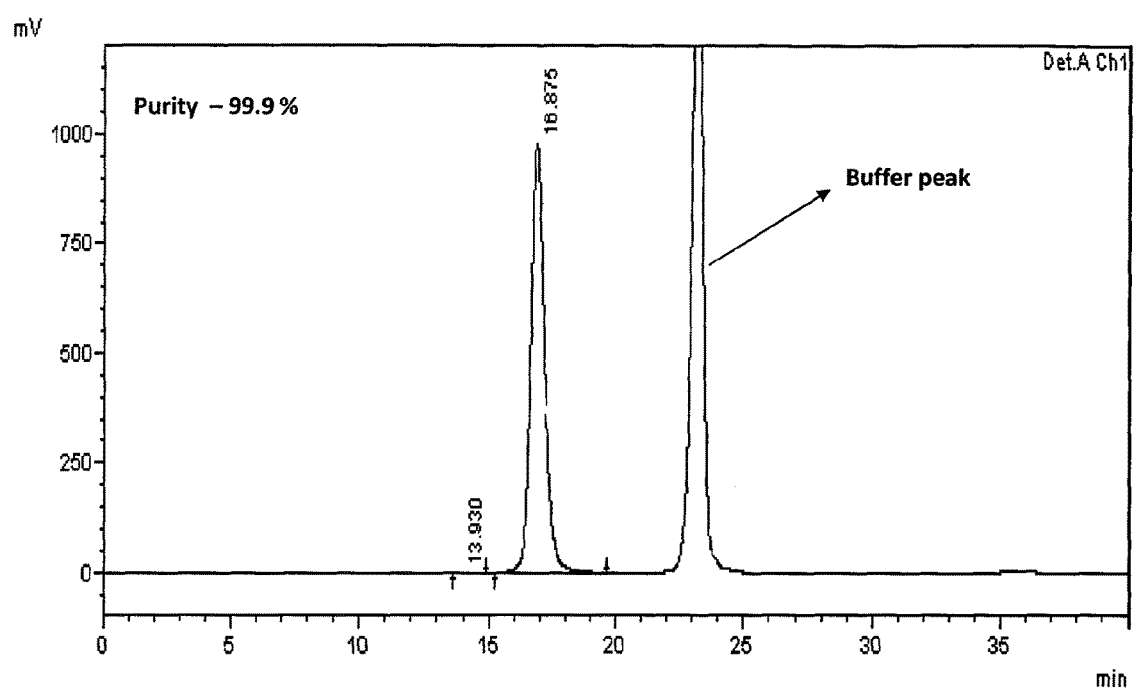
FIG. 9 illustrates the purity of the HIC purified trastuzumab by analytical HP-size exclusion chromatography (HP-SEC). The figure shows that more than 99% purity of trastuzumab is achieved after second column purification.

The purification process for anti-HER2 antibody, Trastuzumab, was carried out in the manner as described in the example 1. The final purified monoclonal antibody exhibits more than 99% purity, as assessed by HP-SEC shown in FIG. 9.

The purified preparation may then be suitably formulated for use as a pharmaceutical substance for human use.

We claim:

1. A process for purification of a monoclonal antibody from cell culture comprising the following steps:
    (a) carrying out affinity chromatography (AF) on the cell culture comprising the monoclonal antibody and collecting eluate comprising the purified monoclonal antibody; and
    (b) carrying out hydrophobic interaction chromatography (HIC) on eluant obtained in (a), optionally followed by other suitable purification steps, wherein hydrophobic interaction chromatography is performed in bind-elute mode.

2. The process as claimed in claim 1, wherein affinity chromatography matrix is selected from protein A, protein G and protein L.

3. The process as claimed in claim 1, wherein affinity chromatography matrix is protein A.

4. The process as claimed in claim 1, wherein step (a) comprises loading of a crude mixture containing the desired antibody to the column at suitable pH and/or conductance for binding, followed by column wash prior to elution of the desired antibody in the form of a single peak.

5. The process as claimed in claim 4, wherein antibody is recovered from the column with buffer components selected from citrate, acetate, and phosphate.

6. The process as claimed in claim 4, wherein antibody is recovered from the column with additive selected from sodium chloride, arginine, and glycine.

7. The process as claimed in claim 4, wherein column wash comprises:
    (i) First wash with equilibration buffer at suitable pH and/or conductivity (ii) Second wash at the same pH as of the first wash buffer and/or a conductivity higher than the first wash buffer (iii) Third wash at a pH and/or a conductivity lower than the second wash buffer (iv) Elution of an antibody at lower pH and/or higher conductivity than third wash buffer.

8. The process as claimed in claim 7, wherein the column wash comprises:
    (i) First wash with equilibration buffer at about pH 7.4 and/or conductivity in the range of 1 mS/cm to 30 mS/cm (ii) Second wash at about pH 7.4 and/or conductivity more than 30 mS/cm (iii) Third wash at pH in the range of pH 5 to pH 6.5 and/or conductivity in the range of 1 mS/cm to 5 mS/cm (iv) Elution of an antibody at about pH 3.5 and/or conductivity higher than 5 mS/cm.

9. The process as claimed in claim 7, wherein equilibration buffer and wash buffer component is selected from tris, acetate and citrate buffer.

10. The process as claimed in claim 7, wherein elution of an antibody is performed at a pH ranging from about pH 3.5 to pH 4.

11. The process as claimed in claim 7, wherein elution is performed with additive in the buffer, wherein the additive is selected from the group consisting of sodium chloride, arginine, and glycine.

12. The process as claimed in claim 7, wherein elution of an antibody is performed at pH in the range of pH 5 to pH 7.

13. The process as claimed in claim 1, wherein an amount of aggregates in an antibody preparation after step (a) is no greater than 5%.

14. The process as claimed in claim 1, wherein step (b) is performed a pH the range of pH 5 to pH 7 and/or conductivity more than 100 mS/cm.

15. The process as claimed in claim 1, wherein in step (b) an antibody is eluted from the column with down-the-gradient salt concentration.

16. The process as claimed in claim 15, wherein salt is selected from ammonium sulphate, sodium chloride, ammonium chloride and sodium sulphate.

17. The process as claimed in claim 1, wherein hydrophobic column matrix is selected from phenyl sepharose, butyl sepharose, and octyl sepharose.

18. A process as claimed in claim 1 comprising the steps of (a) Protein A affinity chromatography (b) Hydrophobic interaction chromatography (c) Ion exchange chromatography.

19. The process as claimed in claim 18, wherein step (a) comprises loading of a crude mixture containing the desired antibody to the column at suitable pH and/or conductance for binding, followed by column wash prior to elution of the desired antibody in the form of a single peak.

20. The process as claimed in claim 18, wherein step (b) is performed at pH in the range of pH 5 to pH 7 and/or conductivity more than 100 mS/cm.

21. The process as claimed in claim 18, wherein the ion exchange chromatography is selected from cation exchange chromatography and anion exchange chromatography.

22. The process as claimed in claim 21, wherein ion exchange chromatography is anion exchange chromatography.

23. The process as claimed in claim 18, wherein the column matrix for anion exchange chromatography is selected from DEAE sepharose, Mono Q and Q sepharose XL.

24. The process as claimed in claim 23, wherein column is Q sepharose.

25. The process as claimed in claim 18, wherein elution of antibody at step (c) is performed in flow-through-and-wash mode or bind-elute mode.

26. A process as claimed in claim 9 consisting of:
    a) Cell separation b) Protein A chromatography c) Low-pH incubation d) Neutralization and reconditioning e) Hydrophobic interaction chromatography f) Ultrafiltration-diafiltration g) Anion exchange chromatography h) Nano-filtration i) Ultrafiltration-diafiltration j) Micro-filtration.

27. The process as claimed in claim 26, wherein step (b) comprises loading of a crude mixture containing the desired antibody to the column at suitable pH and/or conductance for binding, followed by column wash prior to elution of the desired antibody in the form of a single peak.

28. The process as claimed in claim 26, wherein step (b) is performed at pH in the range of pH 5 to pH 7 and/or conductivity more than 100 mS/cm.

29. The process as claimed in claim 26, wherein diafiltration medium is selected from phosphate, acetate, citrate, succinate and combination thereof.

30. The process as claimed in claim 1, wherein the overall recovery of an antibody is in the range of not less than 50.

31. The process as claimed in claim 1, wherein purified antibody preparation contains no more than 1% aggregate.

32. The process as claimed in claim 1, wherein antibody is selected from anti-HER antibody, anti-TNF antibody, anti-VEGF antibody, anti-CD20 antibody, anti-CD52 antibody, anti-RANKL, and anti-IgE antibody.

33. The process as claimed in claim 1, wherein an antibody is selected from trastuzumab, pertuzumab, adalimumab, bevacizumab, ranibizumab, rituximab, bectumomab, and epratuzumab.

34. The process as claimed in claim 1, wherein the antibody is adalimumab, trastuzumab or rituximab.

* * * * *

UNITED STATES PATENT AND TRADEMARK OFFICE
CERTIFICATE OF CORRECTION

PATENT NO. : 9,708,365 B2
APPLICATION NO. : 14/895432
DATED : July 18, 2017
INVENTOR(S) : Mendiratta et al.

Page 1 of 1

It is certified that error appears in the above-identified patent and that said Letters Patent is hereby corrected as shown below:

On the Title Page

In item (71), in "Applicant", in Column 1, Line 2, after "Ahmedabad", insert --, Gujarat--

In item (72), in "Inventors", in Column 1, Line 2, after "Ahmedabad", insert --, Gujarat--

In item (72), in "Inventors", in Column 1, Line 3, after "Ahmedabad", insert --, Gujarat--

In item (72), in "Inventors", in Column 1, Line 4, after "Ahmedabad", insert --, Gujarat--

In item (73), in "Assignee", in Column 1, Line 2, after "Ahmedabad", insert --,--

In the Claims

In Column 9, Line 59, in Claim 9, delete "iris," and insert --Tris,-- therefor

In Column 10, Line 8, in Claim 14, delete "a pH" and insert --at pH in-- therefor In Column 10, Line 41, in Claim 24, after "column", insert --matrix--

In Column 10, Line 46, in Claim 26, delete "claim 9" and insert --claim 1-- therefor In Column 11, Line 6, in Claim 33, after "pertuzumab,", insert --infliximab,--

Signed and Sealed this
Second Day of July, 2019

Andrei Iancu
*Director of the United States Patent and Trademark Office*